United States Patent
Yang et al.

(10) Patent No.: US 11,518,741 B2
(45) Date of Patent: Dec. 6, 2022

(54) BRIVARACETAM INTERMEDIATE, PREPARATION METHOD THEREFOR, AND PREPARATION METHOD FOR BRIVARACETAM

(71) Applicant: SHANGHAI PUYI CHEMICAL CO., LTD., Shanghai (CN)

(72) Inventors: Hanrong Yang, Shanghai (CN); Yantao Qi, Shanghai (CN); Tao Li, Shanghai (CN); Bo Wang, Shanghai (CN)

(73) Assignee: SHANGHAI PUYI CHEMICAL CO., LTD., Shanghai (CN)

( * ) Notice: Subject to any disclaimer, the term of this patent is extended or adjusted under 35 U.S.C. 154(b) by 85 days.

(21) Appl. No.: 16/973,022

(22) PCT Filed: Oct. 30, 2018

(86) PCT No.: PCT/CN2018/112662
§ 371 (c)(1),
(2) Date: Dec. 7, 2020

(87) PCT Pub. No.: WO2019/242192
PCT Pub. Date: Dec. 26, 2019

(65) Prior Publication Data
US 2021/0253523 A1 Aug. 19, 2021

(30) Foreign Application Priority Data
Jun. 20, 2018 (CN) .......................... 201810634229.9

(51) Int. Cl.
| C07D 207/27 | (2006.01) |
| C07C 231/12 | (2006.01) |
| C07C 231/18 | (2006.01) |
| C07C 231/24 | (2006.01) |
| C07C 237/06 | (2006.01) |
| C07D 207/273 | (2006.01) |

(52) U.S. Cl.
CPC .......... *C07D 207/27* (2013.01); *C07C 231/12* (2013.01); *C07C 231/18* (2013.01); *C07C 231/24* (2013.01); *C07C 237/06* (2013.01); *C07D 207/273* (2013.01)

(58) Field of Classification Search
CPC ............................ C07D 207/27; C07C 231/12
See application file for complete search history.

(56) References Cited

U.S. PATENT DOCUMENTS

| 7,629,474 B2 | 12/2009 | Surtees et al. |
| 8,492,416 B2 | 7/2013 | Kenda et al. |
| 2019/0152908 A1 | 5/2019 | Wang et al. |

FOREIGN PATENT DOCUMENTS

| CN | 1208319 C | 6/2005 |
| CN | 1882535 B | 5/2011 |
| CN | 106279074 A | 1/2017 |
| CN | 106748950 A | 5/2017 |
| CN | 107513032 A | 12/2017 |
| CN | 107663185 A | 2/2018 |
| CN | 109593055 A | 4/2019 |
| CN | 110615744 A | 12/2019 |
| WO | 2018220646 A1 | 12/2018 |

OTHER PUBLICATIONS

International Search Report of PCT Application PCT/CN2018/112662 dated Feb. 22, 2019.
Written Opinion of the International Searching Authority of PCT Application PCT/CN2018/112662 dated Feb. 22, 2019.
First Office Action of Japanese patent application 2020-571459.
Jul. 5, 2022 First Chinese Office Action issued in Chinese Patent Application No. 201810634229.9.

*Primary Examiner* — Kamal A Saeed
(74) *Attorney, Agent, or Firm* — Houston Beshining Law Office PLLC; Liangang Ye

(57) ABSTRACT

The present invention relates to a brivaracetam intermediate, a preparation method therefor, and a preparation method for brivaracetam. The steps of the method for preparing brivaracetam described in the present invention are short and the raw materials are cheap, moreover, the method is simple and highly effective without requiring isomer separation by means of column chromatography or asymmetric synthesis, being suitable for industrial large-scale production. In addition, disclosed by the present invention is a compound as shown in formula (II), which may be used for the synthesis of brivaracetam.

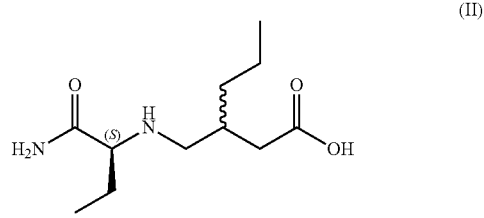

19 Claims, No Drawings

BRIVARACETAM INTERMEDIATE, PREPARATION METHOD THEREFOR, AND PREPARATION METHOD FOR BRIVARACETAM

CROSS REFERENCE TO RELATED APPLICATION

The present application is a National Stage of International Application No. PCT/CN2018/112662, filed on Oct. 30, 2018, which claims priority of the Chinese Patent Application No. CN201810634229.9 filed on Jun. 20, 2018, the contents of which are incorporated herein by reference in their entireties.

FIELD OF INVENTION

The present invention relates to a brivaracetam intermediate, a preparation method therefor, and a preparation method for brivaracetam.

BACKGROUND

Brivaracetam is a new-generation antiepileptic drug developed by UCB. In February 2016, the US FDA approved brivaracetam for the market. Brivaracetam can be used as an additional drug for other drugs in the treatment of partial epilepsy.

The structure of brivaracetam (S)-2-((R)-2-oxo-4-propylpyrrolin-1-yl)butanamide is shown below. Since there are two chiral centers in the brivaracetam, corresponding to four different isomers, this brings certain difficulties to the synthesis of brivaracetam. The current methods for synthesizing brivaracetam are mainly reported as follows.

Brivaracetam

The earliest method, developed by UCB, used n-valeraldehyde as a raw material, first cyclized with glyoxylic acid, and then reacted with L-aminobutanamide, the resulting product was hydrogenated to form a pair of diastereomers, and then separated and purified by the column chromatographic to obtain the product brivaracetam. Such as described in CN1208319C and CN1882535B. Although the steps of this method are short, the last step can only be separated by column chromatography, which is costly and is not suitable for mass production and limits its application.

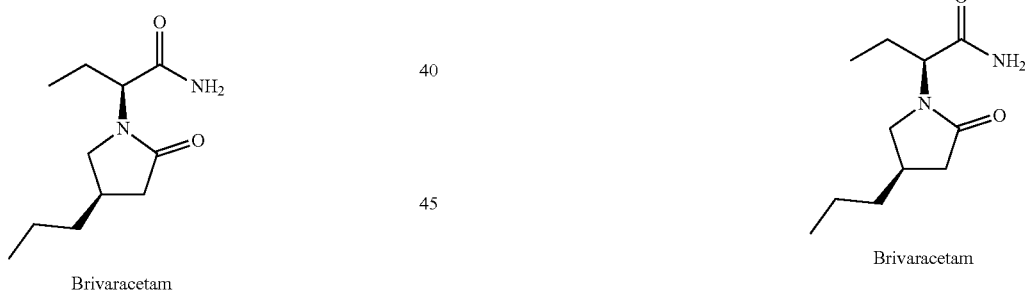

Brivaracetam

CN107663185A reported that (R)-4-propyldihydrofuran-2(3H)-one was used as an intermediate to react with L-aminobutanamide to obtain brivaracetam. However, the synthesis route of chiral (R)-4-propyldihydrofuran-2(3H)-one is very long, involving the reaction of metal reagents, and it also needs multiple conversions with L-aminobutanamide to obtain the target product. This makes the entire synthesis route long and complicated to

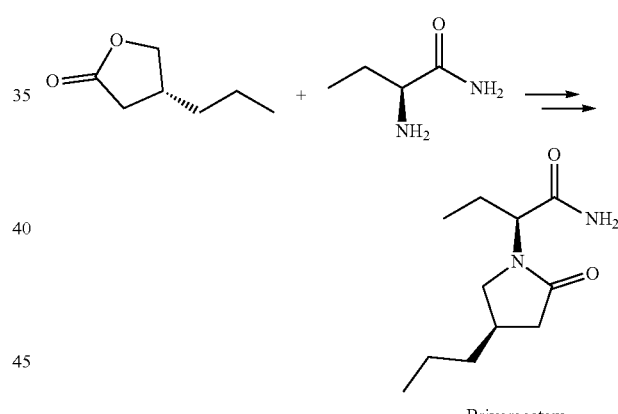

Brivaracetam

CN106748950A reported a method of using a mixture of epimer acid as an intermediate to obtain a single isomer acid through the method of salt formation and purification with R-phenethylamine, and then converting into brivaracetam. This method is relatively simple, but it is difficult to implement in actual operation.

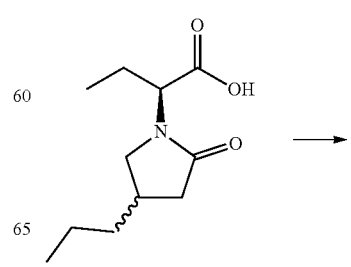

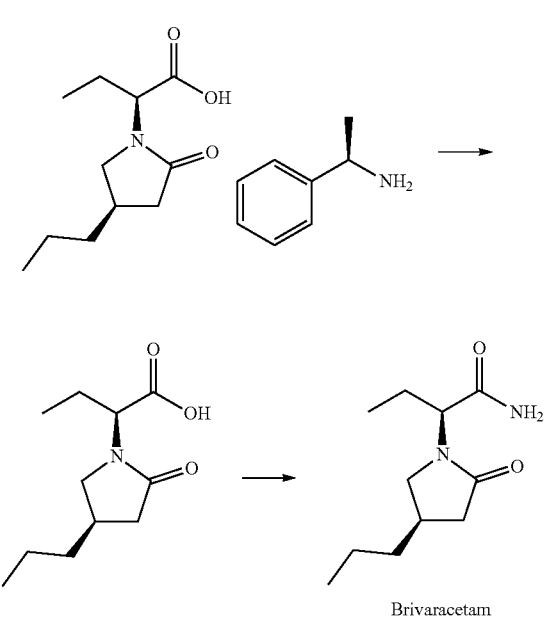

Brivaracetam

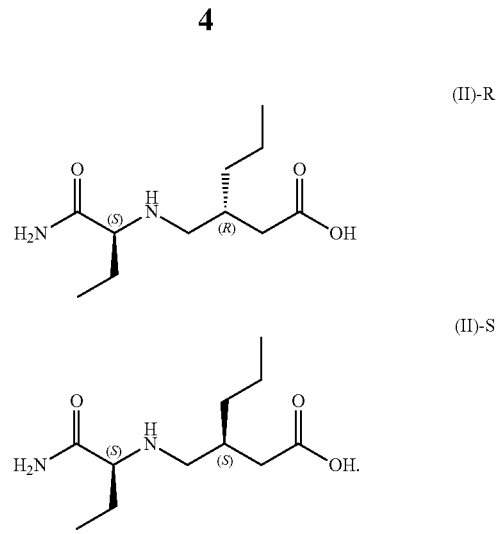

The salt of (R)-3-((((S)-1-amino-1-oxobutan-2-yl)amino)methyl)hexanoic acid and (S)-3-((((S)-1-amino-1-oxobutan-2-yl)amino)methyl)hexanoic acid can be a conventional salt in the art, preferably a salt formed with X, the structure of which is as follows:

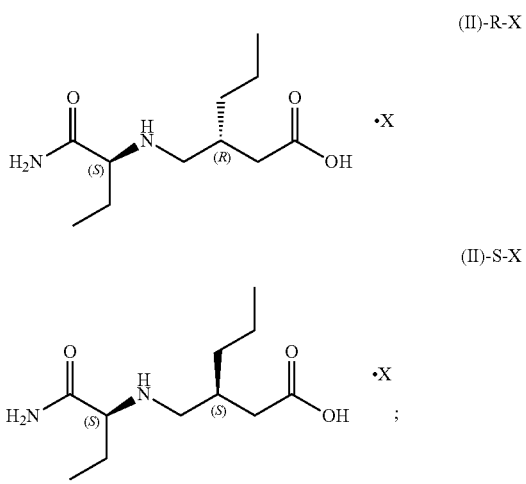

wherein, the X may be a conventional organic acid in the art, preferably oxalic acid or maleic acid.

The salt of (R)-3-((((S)-1-amino-1-oxobutan-2-yl)amino)methyl)hexanoic acid and (S)-3-((((S)-1-amino-1-oxobutan-2-yl)amino)methyl)hexanoic acid may be any one of the following compounds:

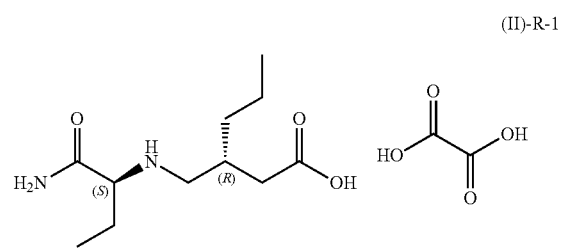

CONTENT OF THE PRESENT INVENTION

The technical problems to be solved by the present invention are to overcome the defects of high cost, long steps, complicated operation, and unsuitable for industrial production in the existing preparation methods of brivaracetam. The present invention provides a brivaracetam intermediate, a preparation method therefor, and a preparation method for brivaracetam. The preparation method uses cheap and easily available n-valeraldehyde as a raw material, has short synthesis steps, and is simple and efficient, which does not require column chromatography to separate isomers or asymmetric synthesis, and is suitable for industrialized large-scale production.

The present invention solves the above-mentioned technical problems through the following embodiments.

The present invention provides a 3-((((S)-1-amino-1-oxobutan-2-yl)amino)methyl)hexanoic acid (II) or a pharmaceutically acceptable salt thereof, the structure of which is as follows:

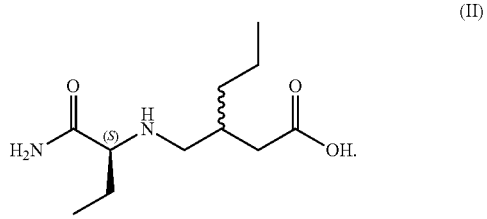

The compound represented by formula (II) is (R)-3-((((S)-1-amino-1-oxobutan-2-yl)amino)methyl)hexanoic acid (abbreviated as (II)-R), (S)-3-((((S)-1-amino-1-oxobutan-2-yl)amino)methyl)hexanoic acid (abbreviated as (II)-S), or a mixture thereof at any ratio;

-continued

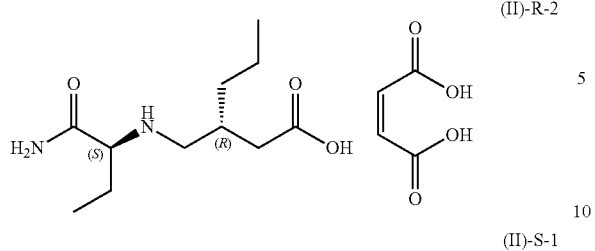
(II)-R-2

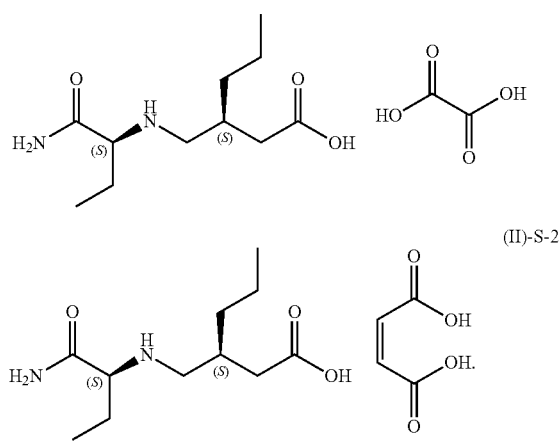
(II)-S-1

(II)-S-2

The present invention provides a method for preparing brivaracetam represented by formula (I), which comprises the following steps: in a solvent, carrying out a cyclization reaction with the compound represented by formula (II)-R-X or (II)-R as shown below; wherein, X is an organic acid;

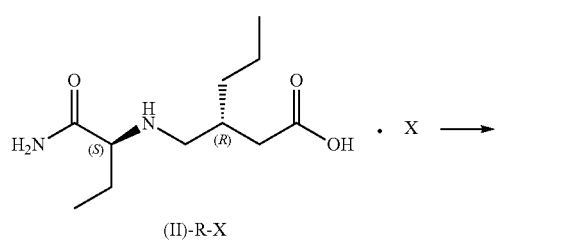
(II)-R-X

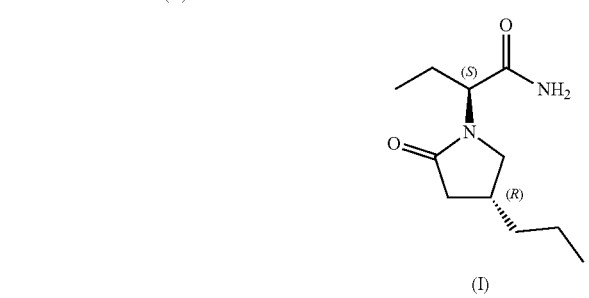
(I)

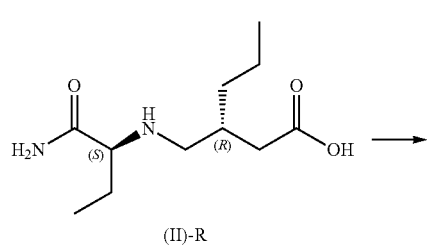
(II)-R

-continued

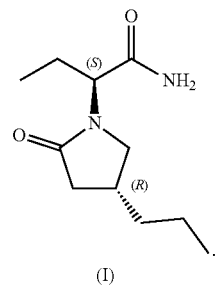
(I)

In the cyclization reaction, X is preferably oxalic acid or maleic acid.

In the cyclization reaction, the solvent is preferably one or more of water, alcohol solvents and thionyl chloride, more preferably $C_{1-4}$ alcohol, and further more preferably one or more of methanol, ethanol and isopropanol.

In the cyclization reaction, the molar concentration of the compound represented by formula (II)-R-X or (II)-R in the solvent may be a conventional molar concentration for such cyclization reactions in the art, and preferably 0.2-1.0 mol/L, more preferably 0.4-0.8 mol/L, such as 0.48 mol/L or 0.72 mol/L.

In the cyclization reaction, the temperature of the cyclization reaction may be conventional temperature for such cyclization reactions in the art, preferably 25-100° C., more preferably 25-80° C., further preferably 65-80° C.

In the cyclization reaction, the progress of the cyclization reaction may be monitored by conventional detection methods (such as HPLC, TLC) for such reactions in the art. Generally, the disappearance of the compound (II)-R-X or (II)-R is seen as the completion of the reaction, and the reaction time is preferably 4-10 h, such as 6 h.

After the completion of the cyclization reaction, preferably, a post-treatment step may be further included. The conditions and operations of the post-treatment may be conventional conditions and operations for such reactions in the art, and preferably comprises the following steps: concentrating, adjusting the pH to 8-9, extracting, drying, and concentrating to obtain a crude product, then recrystallizing the crude product, filtering through suction filtration, washing and drying. The conditions and operations of the concentration may be conventional conditions and operations for such reactions in the art, and concentration under reduced pressure is preferred. The base used for adjusting the pH may be a conventional base for such reactions in the art, preferably sodium carbonate, more preferably 10% sodium carbonate aqueous solution. The conditions and operations of the extraction may be conventional conditions and operations for such reactions in the art. The extraction solvent may be a conventional extraction solvent for such reactions in the art, preferably dichloromethane. The drying conditions and operations may be conventional conditions and operations for such reactions in the art. The conditions and operations of the recrystallization may be conventional conditions and operations for such reactions in the art, and the solvent of the recrystallization may be a conventional solvent for such reactions in the art, preferably ethyl acetate and n-heptane, or ethyl acetate and petroleum ether, and the volume ratio of ethyl acetate to (n-heptane or petroleum ether) is preferably 1:5; the recrystallization time may be a conventional time for such reactions in the art, for example, 1 h. The conditions and operations of the suction filtration may be conventional conditions and operations for such reactions in the art. The conditions and operations of washing may be conventional conditions and operations for such reactions in the art, and the washing solvent is preferably n-heptane or petroleum ether. The conditions and operations of drying may be conventional conditions and operations for such reactions in the art, such as oven drying.

The method for preparing brivaracetam represented by formula (I) may further comprise the following steps: under the action of a base, dissociating the compound represented by formula (II)-RX to obtain the compound represented by formula (II)-R;

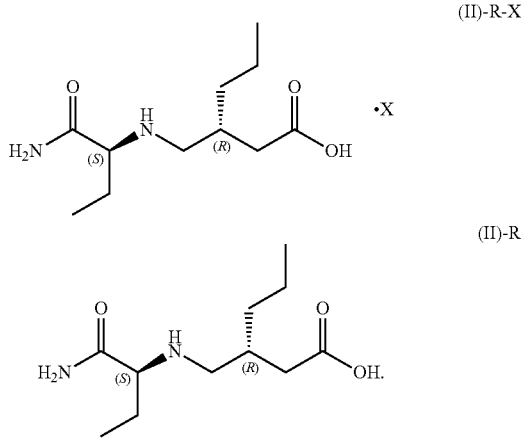

The dissociation conditions and operations are the same as the conventional conditions and operations for such reactions in the art. The base may be a base commonly used for dissociation in the art, such as sodium hydroxide, potassium hydroxide or ammonium hydroxide.

The method for preparing brivaracetam represented by formula (I) may further comprise the following steps: carrying out a salification reaction between the compound represented by formula (II) and X, then crystallizing to obtain the compound represented by formula (II)-R-X; wherein, X is an organic acid;

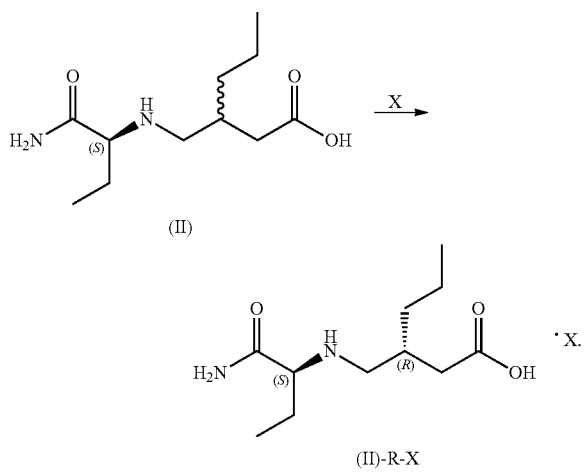

The X is preferably oxalic acid or maleic acid.

In the salification reaction step, the solvent is preferably $C_{1-4}$ alcohol and/or water. The $C_{1-4}$ alcohol is preferably one or more of isopropanol, n-butanol and isobutanol.

When the solvent of the salification reaction step is $C_{1-4}$ alcohol and water, then the mass ratio of the $C_{1-4}$ alcohol to the water is not particularly limited, as long as it does not affect the salification reaction.

In the salification reaction step, the mass ratio of the solvent to the compound represented by formula (II) is preferably (2-10):1, more preferably (3-5):1, and further more preferably 4:1.

The molar ratio of the compound represented by formula (II) to the X may be a conventional molar ratio for such salification reactions in the art, preferably (0.8-2):1, more preferably (1-1.5):1, and furthermore preferably (1-1.3):1, such as 1.1:1.

In the crystallization step, the solvent is preferably a mixed solvent of $C_{1-4}$ alcohol, water and ether solvent, or a mixed solvent of $C_{1-4}$ alcohol, water and alkane solvent. The $C_{1-4}$ alcohol is preferably one or more of isopropanol, n-butanol and isobutanol. The ether solvent is preferably petroleum ether and/or isopropyl ether. The alkane solvent is preferably n-hexane and/or n-heptane.

In the crystallization step, the solvent is preferably a mixed solvent of n-butanol, water and isopropyl ether, a mixed solvent of isobutanol, water and isopropyl ether, a mixed solvent of isobutanol, water and petroleum ether, a mixed solvent of n-butanol, water and n-heptane, a mixed solvent of isopropanol, water and isopropyl ether, or a mixed solvent of isopropanol, water and n-hexane, more preferably a mixed solvent of isobutanol, water and isopropyl ether, or a mixed solvent of isopropanol, water and isopropyl ether.

In the crystallization step, the mass ratio of the $C_{1-4}$ alcohol, water and (ether solvent or alkane solvent) is preferably (2-10): 1:(2-10), more preferably (3-5):1:(4-6), more preferably 4:1:(4-6), for example 4:1:4 or 4:1:6.

In the crystallization step, the mass ratio of the solvent to the compound represented by formula (II) is preferably (5-15):1, more preferably (7-11):1, such as 9:1 or 11:1.

The temperature of the crystallization is preferably 5-50° C., more preferably 10-40° C., and further preferably 25-30° C.

In the crystallization step, the crystallization time may refer to the time conventionally required for crystallization in the art, preferably 0.5-5 h, more preferably 1-2 h.

The number of times of the crystallization step is not particularly limited, as long as SR:SS≥99.0:1.0 may be achieved, for example, 2 times, 3 times.

In a preferred embodiment of the present invention, adding the compound represented by formula (II) to a mixed solvent of $C_{1-4}$ alcohol and water, and then adding an organic acid, ether or alkane solvent in sequence, and crystallizing.

Ina preferred embodiment of the present invention, adding the compound represented by formula (II) to a mixed solvent of $C_{1-4}$ alcohol and water, and then adding an organic acid, ether or alkane solvent in sequence, and crystallizing. The product obtained by crystallization is added to a mixed solvent of $C_{1-4}$ alcohol and water, and then ether or alkane solvent is added to crystallize.

After the crystallization is completed, preferably, it may further include a post-treatment operation. The conditions and operations of the post-treatment may be conventional conditions and operations for such reactions in the art, and preferably may comprise the following steps: filtering by suction filtration, washing, and drying. The conditions and operations of the suction filtration may be conventional conditions and operations for such reactions in the art. The conditions and operations of the washing may be conventional conditions and operations for such reactions in the art.

The solvent of washing is preferably ether solvents and/or alkane solvents, more preferably isopropyl ether, petroleum ether, n-hexane or n-heptane. The conditions and operations of the drying may be conventional conditions and operations for such reactions in the art, and the drying temperature may be a conventional temperature for such reactions in the art, for example, 65° C.; the reaction time for drying is a conventional time for such reactions in the art, for example, 12 h.

The method for preparing brivaracetam represented by formula (I) may further comprise the following steps: in a solvent, under the action of a catalyst, carrying out a hydrogenation reduction reaction between the compound represented by formula (III) and hydrogen as shown below to obtain the compound represented by formula (II);

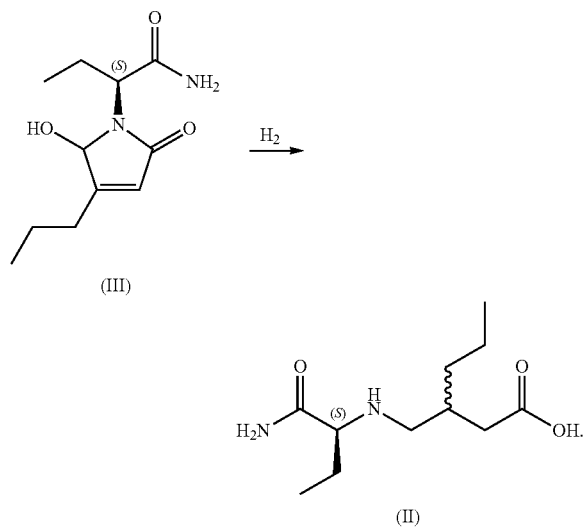

In the hydrogenation reduction reaction, the solvent is preferably water and/or $C_{1-4}$ alcohol. The $C_{1-4}$ alcohol is preferably one or more of ethanol, isopropanol, n-butanol and isobutanol.

In the hydrogenation reduction reaction, the catalyst may be a conventional catalyst for such hydrogenation reduction reactions in the art, preferably Pd/C.

In the hydrogenation reduction reaction, the pressure of the hydrogen is preferably 1-30 bar, more preferably 5-20 bar.

In the hydrogenation reduction reaction, the mass ratio of the catalyst to the compound represented by formula (III) may be a conventional mass ratio for such hydrogenation reduction reactions in the art, preferably 0.05:1-0.15:1, more preferably 0.1:1.

In the hydrogenation reduction reaction, the molar concentration of the compound represented by formula (III) in the solvent may be a conventional molar concentration for such hydrogenation reduction reactions in the art, preferably 0.1-0.8 mol/L, more preferably 0.3-0.5 mol/L, for example 0.44 mol/L.

In the hydrogenation reduction reaction, the reaction temperature may be a conventional temperature for such hydrogenation reduction reactions in the art, preferably 10-50° C., more preferably 20-30° C., for example 25° C.

In the hydrogenation reduction reaction, the progress of the reaction may be monitored by the conventional detection methods (such as HPLC, TLC) for such hydrogenation reduction reactions in the art. Generally, the disappearance of the compound III is seen as the completion of the reaction, and the reaction time is preferably 8-24 h, and more preferably 16-20 h, for example 18 h.

The hydrogenation reduction reaction is preferably carried out with the participation of an organic acid, and the organic acid is preferably one or more of citric acid, oxalic acid and maleic acid, more preferably citric acid. The molar ratio of the organic acid to the compound represented by formula (III) is preferably (7-10):1, for example 8.4:1.

After the hydrogenation reduction reaction is completed, preferably, it may further include a post-treatment operation. The conditions and operations of the post-treatment may be conventional conditions and operations for such reactions in the art, and preferably comprises the following steps: filtering and concentrating. The conditions and operations of filtration may be conventional conditions and operations for such reactions in the art. The conditions and operations of the concentration may be conventional conditions and operations for such reactions in the art, and concentration under reduced pressure is preferred.

The method for preparing brivaracetam represented by formula (I) may further comprise the following steps: in a solvent, carrying out a reaction between the compound represented by formula (IV) and L-aminobutanamide as shown below to obtain the compound represented by formula (III),

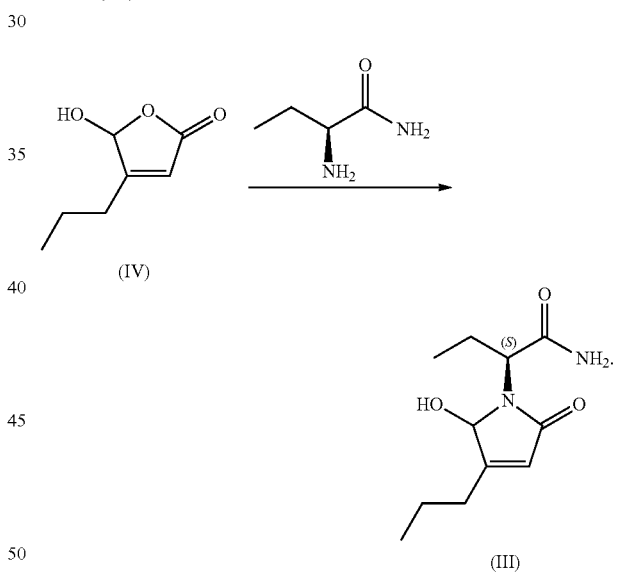

The solvent may be a conventional solvent in the art, preferably alcohol solvent; the alcohol solvent is preferably $C_{1-4}$ alcohol, such as isopropanol.

The concentration of the L-aminobutanamide in the solvent may be a conventional concentration in the art, for example, 1-2 mol/L.

The temperature of the reaction may be a temperature conventional in the art, for example, 30-40° C.

The progress of the reaction may be monitored by the conventional detection methods (such as HPLC, TLC) for such reactions in the art. Generally, the disappearance of the compound IV is seen as the completion of the reaction, and the reaction time is, for example, 1-4 h, and for example, 2-4 h.

The L-aminobutanamide is preferably L-aminobutanamide hydrochloride. Preferably, dissociating the L-aminobutanamide hydrochloride into L-aminobutanamide in ammonia gas atmosphere, and then reacting with the compound represented by formula (IV). The reaction time is judged according to the pH value of the system, and it is preferable to react to a pH of 9-10.

The method of adding the compound represented by formula (IV) is not particularly limited, as long as it does not affect the reaction, and it may be added at once or in batches.

After the reaction is completed, preferably, it may further include a post-treatment operation. The conditions and operations of the post-treatment may be conventional conditions and operations for such reactions in the art, and preferably comprises the following steps: filtering, cooling, crystallizing, filtering, and washing. The conditions and operations of the filtration may be conventional conditions and operations for such reactions in the art, and suction filtration is preferred. The conditions and operations of the crystallization may be conventional conditions and operations for such reactions in the art, and the crystallization temperature is preferably 0-5° C. The conditions and operations of the washing may be conventional conditions and operations for such reactions in the art, and the washing solvent may be a conventional washing solvent for such reactions in the art, preferably ethyl acetate.

The present invention provides a method for preparing a compound represented by formula (II)-R-X, which comprises the following steps: carrying out a salification reaction between the compound represented by formula (II) and X and crystallizing to obtain the compound represented by formula (II)-R-X; wherein, X is an organic acid;

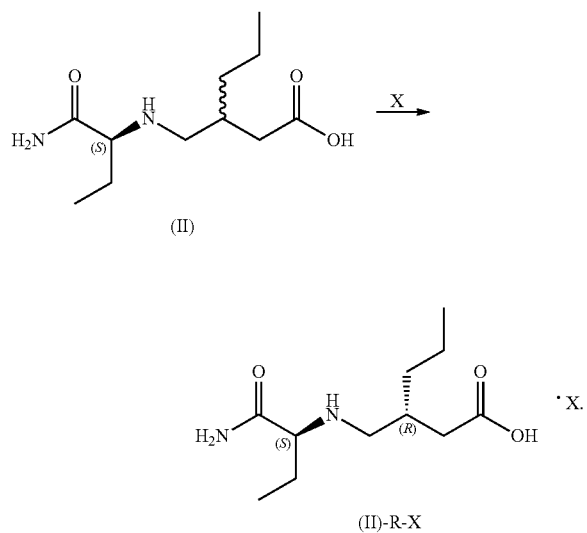

The conditions and operations of the salification reaction and crystallization are the same as those defined above.

The present invention provides a method for preparing a compound represented by formula (II)-S-X, which comprises the following steps:

(i) carrying out a salification reaction between the compound represented by formula (II) and X and crystallizing to obtain the compound represented by formula (II)-R-X;
(ii) adding X and solvent to the mother liquor after crystallization in step (i), and crystallizing;

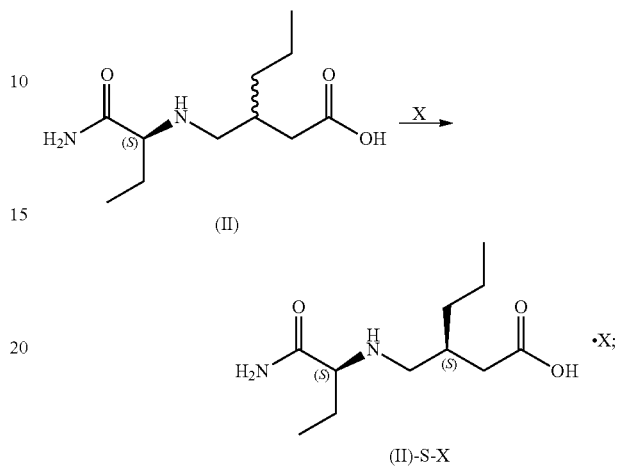

wherein, the X is an organic acid, preferably oxalic acid or maleic acid.

In step (i), the conditions and operations of salification reaction and crystallization are the same as those defined above.

In step (ii), the solvent is preferably ether solvent, more preferably petroleum ether and/or isopropyl ether.

In step (ii), the molar ratio of the X to the compound represented by the formula (II) is preferably 1:(1-4), for example 1:2.

In step (ii), the volume-to-mass ratio of the solvent to the compound represented by formula (II) is preferably (1-4) mL/g, for example, 2 mL/g.

In step (ii), the temperature of the crystallization is preferably −20-0° C., for example −10° C.

In step (ii), the time for the crystallization may refer to a time conventionally required for crystallization in the art, such as 0.5-5 h, e.g., 2-4 h.

After step (ii) is completed, preferably, it may further comprise a post-treatment operation. The conditions and operations of the post-treatment may be conventional conditions and operations for such reactions in the art, and preferably comprise the following steps: filtering, washing, and drying. The conditions and operations of the filtration may be conventional conditions and operations for such reactions in the art, and suction filtration is preferred. The conditions and operations of the washing may be conventional conditions and operations for such reactions in the art, and the solvent of the washing is preferably ether solvent, such as petroleum ether and/or isopropyl ether. The conditions and operations of the drying may be conventional conditions and operations for such reactions in the art, the drying temperature may be a conventional temperature in the art, such as 50° C., and the drying time may be a conventional time in the art, for example 12 h.

The present invention provides a method for preparing a compound represented by formula (II), which comprises the following steps: in a solvent, under the action of a catalyst, carrying out a hydrogenation reduction reaction between the compound represented by formula (III) and hydrogen as shown below to obtain the compound represented by formula (II);

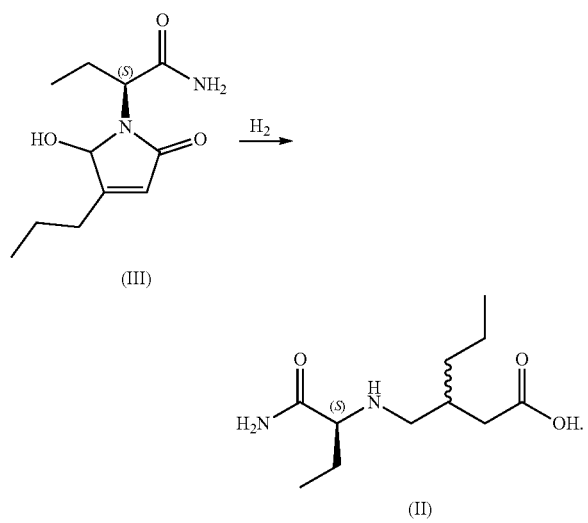

(III)

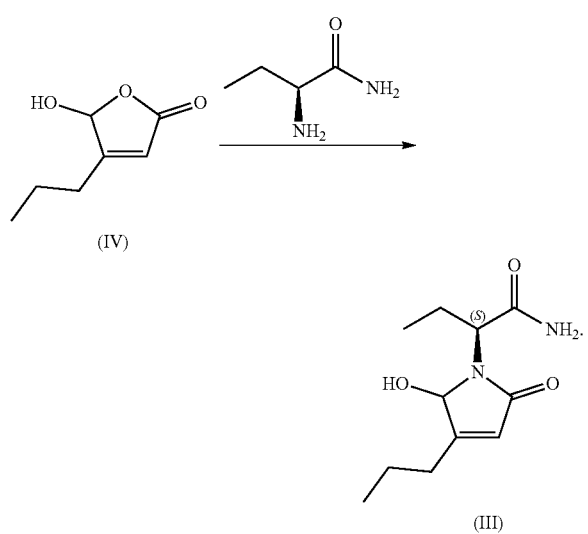

(II)

The conditions and operations of the hydrogenation reduction reaction are the same as those defined above.

The method for preparing a compound represented by formula (II) may further comprise the following steps: in a solvent, carrying out a reaction between the compound represented by formula (IV) and L-aminobutanamide as shown below to obtain the compound represented by formula (III),

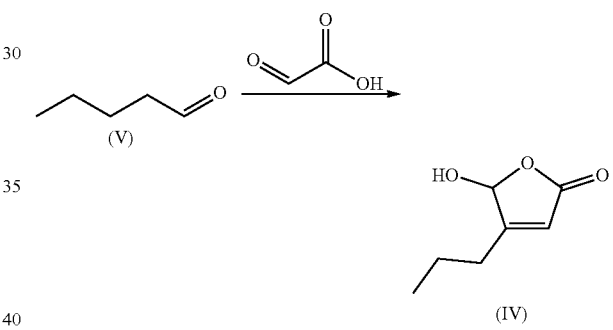

The conditions and operations of the reaction are the same as those defined above.

If the temperature is not particularly emphasized, it usually means that the reaction is carried out at room temperature. The room temperature in the present invention refers to 20-30° C.

On the basis of not violating common knowledge in the art, the above-mentioned preferred conditions may be combined arbitrarily to obtain preferred embodiments of the present invention.

Unless otherwise specified, the reagents and raw materials used in the present invention are commercially available.

The positive and progressive effects of the present invention are:

the present invention uses cheap and easily available n-valeraldehyde and glyoxylic acid as raw materials, and the generated product does not need to be separated by column chromatography, and at the same time, no metal reagents are required in the reaction process. The synthesis route of brivaracetam of the present invention has short steps and cheap raw materials, and is simple and efficient, which does not require column chromatography to separate isomers or asymmetric synthesis, reduces production costs, and is suitable for industrialized large-scale production.

DETAILED DESCRIPTION OF THE PREFERRED EMBODIMENT

In order to better understand the content of the present invention, further description will be given below in conjunction with specific embodiments. It should be understood that the following examples further illustrate the present invention, but the present invention is not limited thereto. The isomer ratios mentioned in the following examples are all measured by HPLC.

Example 1: preparation of
5-hydroxy-4-propylfuran-2(5H)-one (IV)

125 mL of n-heptane and 30 mL of morpholine were added to a three-necked flask, and the mixture was stirred at room temperature for 10 minutes and mixed evenly, then the temperature was cooled to below 4° C. and 25.0 g of 50% glyoxylic acid aqueous solution was added dropwise. After the addition, the temperature was raised to 25-30° C. and stirred to react for 2 h, then 30.5 g of n-valeraldehyde was slowly added below 40° C., and the mixture was continued to stir and react for 18 h. After the reaction was completed, the temperature was lowered to 20° C., and 21.3 g of concentrated hydrochloric acid was slowly added dropwise and stirred.

Then the mixture was cooled to room temperature and was kept standing to remove the n-heptane phase. 100 mL of ethyl acetate was added to the aqueous phase, and then the pH of which was adjusted to 4 by adding sodium carbonate solid slowly, and the organic phase was separated, and then extracted with ethyl acetate. The combined organic phase was washed with saturated brine, dried over anhydrous sodium sulfate and filtered by suction filtration and concentrated under reduced pressure to obtain 43.9 g of 5-hydroxy-4-propylfuran-2(5H)-one (IV) as a brown oil with a yield of 91.5%. $^1$H NMR (400 MHz, Chloroform-d) δ 0.93-1.00 (t, 3H), 1.56-1.67 (q, 2H), 2.31-2.43 (q, 2H), 5.81 (s, 1H), 6.02 (s, 1H). MS (ESI) m/z=143 (M+H)$^+$.

Example 2: preparation of (2S)-2-(2-hydroxy-5-oxo-3-propyl-2,5-dihydro-1H-pyrrol-1-yl)butanamide

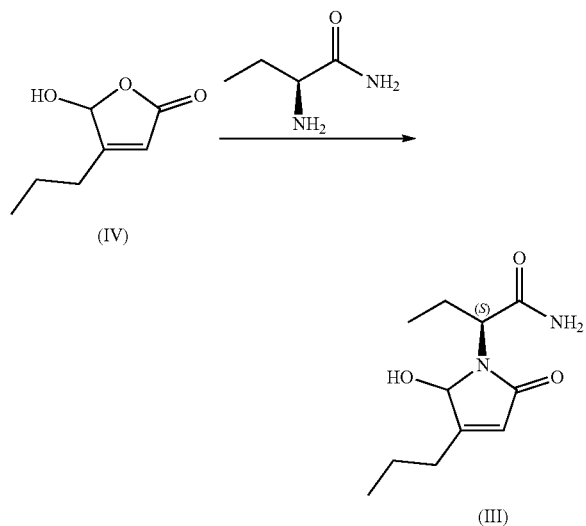

96.2 g of aminobutanamide hydrochloride was mixed with 1000 mL of isopropanol, and ammonia gas was used for dissociation until the pH value of the system was 9-10, and the pH value did not change. The salt was removed by filtration, and the filtrate was concentrated to 500 mL for later use.

98.4 g of 5-hydroxy-4-propylfuran-2(5H)-one (IV) was added in batches to the above 500 mL of aminobutanamide solution, and the temperature was controlled at 30-40° C. to react for more than 2 hours. After the reaction was completed, the salt was removed by filtration, and the filtrate was slowly cooled to 0-5° C. for crystallization, then filtered by suction filtration, and rinsed with a small amount of ethyl acetate to obtain 139.2 g of (2S)-2-(2-hydroxy-5-oxo-3-propyl-2,5-dihydro-1H-pyrrol-1-yl) butanamide (HI) as a white solid with a yield of 88.8%. $^1$H NMR (500 MHz, Chloroform-d) δ 6.45 (s, 1H), 5.89 (s, 1H), 5.85 (s, 1H), 5.57 (s, 1H), 3.42 (s, 1H), 2.39 (s, 3H), 1.82 (dq, J=14.4, 7.4, 6.9 Hz, 1H), 1.74 (dt, J=14.2, 7.2 Hz, 1H), 1.67 (dd, J=14.6, 7.2 Hz, 2H), 1.02 (dt, J=11.3, 7.4 Hz, 6H). MS (ESI) m/z=227 (M+H)$^+$.

Example 3: preparation of 3-((((S)-1-amino-1-oxobutan-2-yl)amino) methyl)hexanoic acid (II)

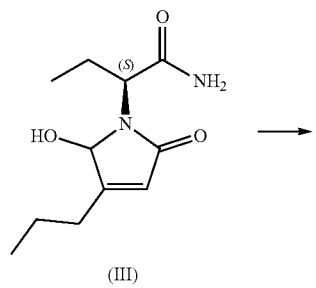

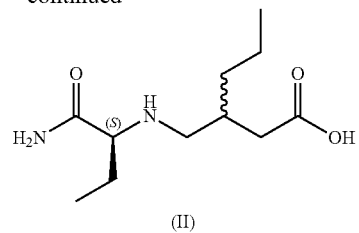

15.0 g of (2S)-2-(2-hydroxy-5-oxo-3-propyl-2,5-dihydro-1H-pyrrol-1-yl) butanamide (II) was added to 150 mL of water, and 1.5 g of citric acid and 1.5 g of 5% Pd/C were added, the mixture was stirred evenly, and it was replaced with nitrogen gas. Hydrogen gas was added until the pressure was 20 bar, and the mixture was stirred and reacted overnight at room temperature. After the reaction was completed, the Pd/C was removed by filtration, and the filtrate was dried by rotary evaporation below 50° C. to obtain 16.3 g of 3-((((S)-1-amino-1-oxobutan-2-yl)amino)methyl) hexanoic acid (1) as a pale yellow oil with a yield of 93.7%. $^1$H NMR (400 MHz, DMSO-d$_6$) δ 7.34 (s, 1H), 7.01 (s, 1H), 2.96-2.79 (m, 1H), 2.56 (dd, J=11.6, 4.9 Hz, 1H), 2.40 (d, J=4.8 Hz, 1H), 2.29 (ddt, J=28.6, 20.1, 10.3 Hz, 1H), 2.13 (ddd, J=21.1, 11.9, 5.2 Hz, 1H), 1.93-1.74 (m, 1H), 1.49 (tt, J=13.6, 6.5 Hz, 2H), 1.41-1.07 (m, 4H), 0.82 (dt, J=29.2, 6.6 Hz, 6H). MS (ESI) m/z=231 (M+H)$^+$.

The above reduction reaction operations were repeated using different solvents, organic acids and hydrogen pressures, and after 18 hours of reaction at room temperature (25° C.), the yield was calculated respectively. The experimental results were shown in Table 1:

TABLE 1

| NO. | Solvents | Organic acids | Hydrogen pressure | Yield |
|---|---|---|---|---|
| 1 | Water | None | 20 bar | 78.2% |
| 2 | Water | Citric acid | 20 bar | 93.7% |
| 3 | Water | Oxalic acid | 20 bar | 71.5% |
| 4 | Water | Citric acid | 5 bar | 83.3% |
| 5 | Ethanol | Citric acid | 20 bar | 67.5% |
| 6 | Isopropanol | Citric acid | 20 bar | 74.0% |
| 7 | n-Butanol | Citric acid | 20 bar | 73.1% |
| 8 | Isobutanol | Maleic acid | 20 bar | 66.4% |
| 9 | Isopropanol:water = 1:1 | Citric acid | 20 bar | 84.2% |
| 10 | n-Butanol:water = 2:1 | Citric acid | 20 bar | 81.8% |

Example 4: preparation of (R)-3-((((S)-1-amino-1-oxobutan-2-yl)amino)methyl)hexanoic acid oxalate (II)-R-1

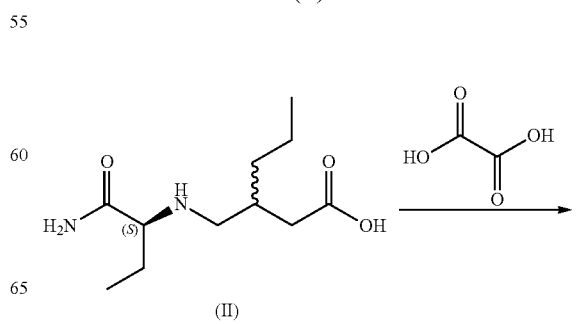

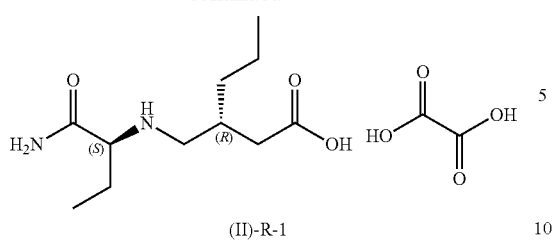

(II)-R-1

100 g of 3-((((S)-1-amino-1-oxobutan-2-yl)amino)methyl)hexanoic acid (II) was dissolved in a mixed solvent containing 400 g of isobutanol and 100 g of water, then 35.2 g of oxalic acid was added to form a salt, and 435 g of isopropyl ether was added dropwise, then it was stirred at 25-30° C. and crystallized for 1-2 hours, then the mixture was filtered by suction filtration, and the solid was rinsed with isopropyl ether, and dried at 65° C. for 12 hours to obtain 100 g of white solid with an isomer ratio of SR:SS=80:20.

The above 100 g white solid was dissolved with 4 times the weight of isobutanol and 1 time the weight of water, and 4 times the weight of isopropyl ether was added dropwise to crystallize, and the operation was repeated twice to obtain 28.5 g of (R)-3-((((S)-1-amino-1-oxobutan-2-yl)amino)methyl)hexanoic acid oxalate (II)-R-1 as a white solid with an isomer ratio of SR:SS=99.8:0.2 and a yield of 20.5%. $^1$H NMR (400 MHz, DMSO-d$_6$) δ 8.05 (s, 1H), 7.65 (s, 1H), 3.63 (t, J=6.3 Hz, 1H), 2.85 (t, J=9.6 Hz, 1H), 2.78-2.61 (m, 1H), 2.43 (dd, J=16.5, 5.8 Hz, 1H), 2.25 (dd, J=16.5, 6.6 Hz, 1H), 2.10 (s, 1H), 1.78 (ddt, 0.1=30.3, 15.3, 7.9 Hz, 2H), 1.57-1.11 (m, 4H), 0.87 (dd, J=13.7, 7.1 Hz, 6H). MS (ESI) m/z=231 (M+H)$^+$.

The above operations were repeated using different solvent systems for crystallization (3 times for crystallizations), and the experimental results were shown in Table 2:

TABLE 2

| NO. | Solvent systems | SR:SS | Yield |
| --- | --- | --- | --- |
| 1 | Isobutanol:water:isopropyl ether = 4:1:4 | 99.8:0.2 | 20.5% |
| 2 | n-Butanol:water:isopropyl ether = 4:1:4 | 99.5:0.5 | 18.8% |
| 3 | Isobutanol:water:n-heptane = 4:1:4 | 99.0:1.0 | 22.3% |
| 4 | Isobutanol:water:petroleum ether = 4:1:4 | 99.1:0.9 | 16.3% |
| 5 | n-Butanol:water:isopropyl ether = 4:1:4 | 99.8:0.2 | 12.5% |
| 6 | Isopropanol:water:isopropyl ether = 4:1:6 | 99.9:0.1 | 10.5% |
| 7 | Isopropanol:water:n-hexane = 4:1:6 | 99.4:0.6 | 13.5% |

Example 5: Preparation of Brivaracetam (I)

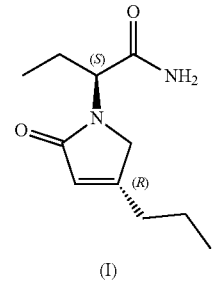

(I)

9.3 g of (R)-3-((((S)-1-amino-1-oxobutan-2-yl)amino)methyl)hexanoic acid oxalate (II)-R-1 with an isomer ratio of SR:SS=99.8:0.2 was dissolved in 6 mL of isopropanol, and the mixture was heated to reflux for 6 hours and cooled down, and concentrated under reduced pressure; and the obtained concentrated solution was adjusted to pH8-9 with 10% sodium carbonate aqueous solution, then extracted with dichloromethane, dried and concentrated to obtain 6.1 g of crude product.

The crude product was dissolved in 6.0 mL of ethyl acetate, and 30 mL of n-heptane was added dropwise, and the mixture was stirred at room temperature for 1 hour to crystallize, then filtered with suction filtration, and washed with n-heptane, and dried to obtain 5.5 g of brivaracetam (I) with an isomer ratio of SR:SS=99.8:0.2 and a yield of 89.3%. $^1$H NMR (400 MHz, CDCl$_3$) δ 6.53 (s, 1H), 5.89 (s, 11H), 4.43 (dd, J=9.0, 6.8 Hz, 1H), 3.44 (dd, J=9.8, 7.9 Hz, 1H), 3.01 (dd, J=9.8, 7.1 Hz, 1H), 2.52 (dd, J=16.7, 8.6 Hz, 1H), 2.35-2.18 (m, 1H), 2.04 (dd, J=16.7, 8.1 Hz, 1H), 1.87 (dd, J=14.2, 7.1 Hz, 1H), 1.74-1.47 (m, 1H), 1.43-1.33 (m, 2H), 1.27 (ddd, J=11.4, 8.2, 5.8 Hz, 2H), 0.85 (dd, J=13.6, 7.3 Hz, 6H). MS (ESI) m/z=213 (M+H)$^+$.

The above operations was repeated using different conditions for cyclization reaction, and the experimental results were shown in Table 3:

TABLE 3

| NO. | Solvents | Temperature | Yield |
| --- | --- | --- | --- |
| 1 | Isopropanol | 80° C. | 89.3% |
| 2 | Methanol | 65° C. | 82.8% |
| 3 | Ethanol | 80° C. | 93.3% |
| 4 | Thionyl Chloride | 25° C. | 77.6% |

Example 6: preparation of (R)-3-((((S)-1-amino-1-oxobutan-2-yl)amino)methyl)hexanoic acid maleate (II)-R-2

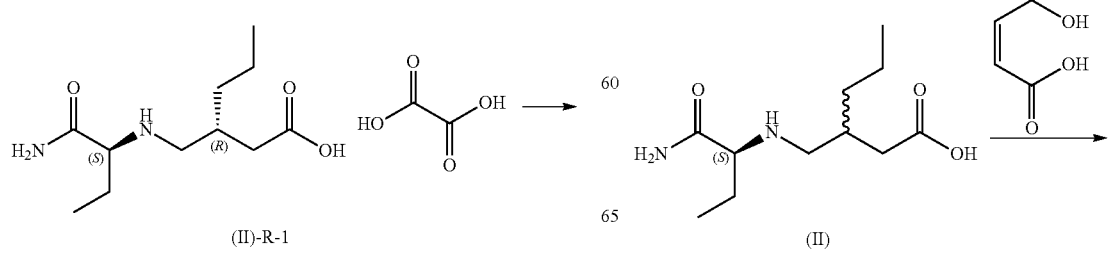

(II)-R-1                              (II)

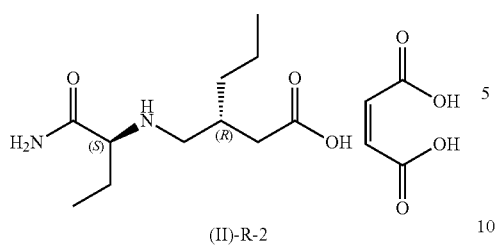

(II)-R-2

100 g of 3-((((S)-1-amino-1-oxobutan-2-yl)amino) methyl)hexanoic acid (II) was dissolved in a mixed solvent containing 400 g of n-butanol and 100 g of water, then 45.4 g of maleic acid was added to form a salt, and 290 g of isopropyl ether was added dropwise, then the mixture was stirred at 25-30° C. and crystallized for 1-2 hours, then it was filtered by suction filtration, and the solid was rinsed with isopropyl ether, and dried at 65° C. for 12 hours to obtain 88 g of white solid with an isomer ratio of SR:SS=76:24.

The above 88 g white solid was dissolved with 4 times the weight of n-butanol and 1 time the weight of water, and 4 times the weight of isopropyl ether was added dropwise to crystallize, and repeated twice to obtain 21.8 g of (R)-3-((((S)-1-amino-1-oxobutan-2-yl)amino)methyl)hexanoic acid maleate (II)-R-2 as a white solid with an isomer ratio of SR:SS=99.6:0.4 and a yield of 14.5%. $^1$H NMR (400 MHz, DMSO-d$_6$) δ 7.98 (s, 1H), 7.73 (s, 1H), 6.04 (s, 2H), 3.83-3.58 (m, 1H), 3.02-2.66 (m, 2H), 2.27 (dd, J=16.6, 6.5 Hz, 1H), 2.11 (s, 1H), 1.80 (ddt, J=29.9, 15.0, 7.5 HZ, 2H), 1.32 (d, J=42.8 Hz, 4H), 0.90 (dd, J=17.2, 8.5 Hz, 6H). MS (ESI) m/z=231 (M+H)$^+$.

The above operations were repeated using different solvent systems for crystallization (3 times for crystallizations), and the experimental results were shown in Table 4:

TABLE 4

| NO. | Solvent systems | SR:SS | Yield |
|---|---|---|---|
| 1 | N-butanol:water:isopropyl ether = 4:1:4 | 99.6:0.4 | 14.5% |
| 2 | Isobutanol:water:isopropyl ether = 4:1:4 | 99.7:0.3 | 17.8% |
| 3 | Isobutanol:water:petroleum ether = 4:1:4 | 99.5:0.5 | 11.1% |
| 4 | n-Butanol:water:n-heptane = 4:1:6 | 99.1:0.9 | 20.3% |
| 5 | Isopropanol:water:isopropyl ether = 4:1:6 | 99.8:0.2 | 9.6% |
| 6 | Isopropanol:water:n-hexane = 4:1:6 | 99.5:0.5 | 11.7% |

Example 7: Preparation of Brivaracetam (I)

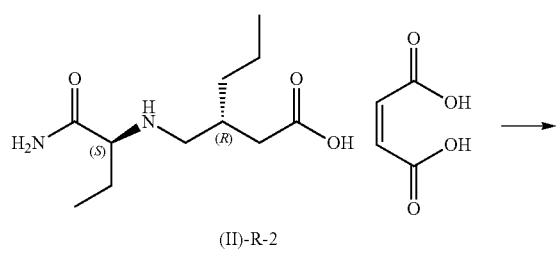

(II)-R-2

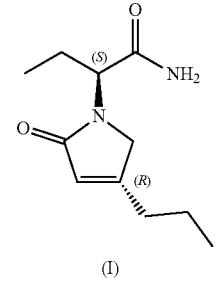

(I)

10.0 g of (R)-3-((((S)-1-amino-1-oxobutan-2-yl)amino) methyl)hexanoic acid maleate (II)-R-2 with an isomer ratio of SR:SS=99.7:0.3 was dissolved in 60 mL of ethanol, and the mixture was heated to reflux for 6 hours and cooled, then concentrated under reduced pressure; the pH of the concentrated solution was adjusted to 8-9 with 10% sodium carbonate aqueous solution, and then extracted with dichloromethane, and the extraction liquid was dried and concentrated to obtain 5.5 g of crude product.

The crude product was dissolved in 6.0 mL of ethyl acetate, and 30 mL of petroleum ether was added dropwise, and the mixture was stirred at room temperature for 1 hour to crystallize, then it was filtered by suction filtration, and rinsed with petroleum ether, and dried to obtain 5.0 g of brivaracetam (I) with an isomer ratio of SR:SS=99.7:0.3 and a yield of 81.6%. See Example 5 for structural identification data.

Example 8: preparation of (S)-3-((((S)-1-amino-1-oxobutan-2-yl)amino)methyl)hexanoic acid maleate (II)-S-2

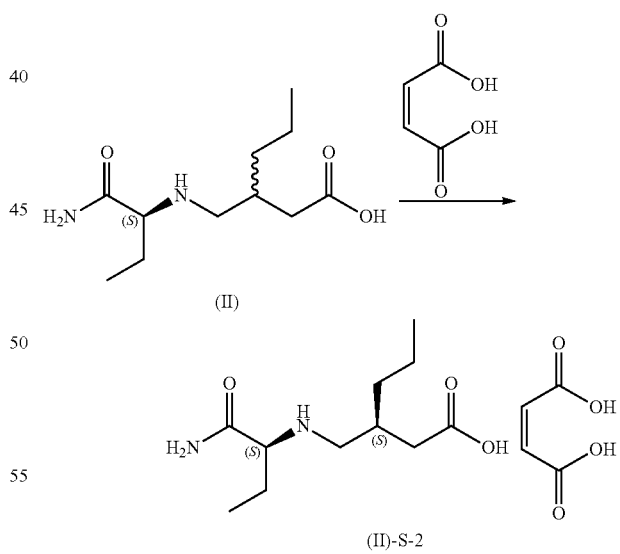

(II)

(II)-S-2

The mother liquor obtained from the resolution in example 6 was added into a reaction flask, and 25.3 g of maleic acid was added, then 200 mL of isopropyl ether was added dropwise, and the mixture was stirred and the temperature was cooled to −10° C. to crystallize for 3 hours, then filtered by suction filtration at a low temperature, and rinsed with isopropyl ether and dried for 12 hours at 50° C. to obtain 16.2 g of (R)-3-((((S)-1-amino-1-oxobutan-2-yl)

amino)methyl)hexanoic acid maleate (II)-S-2 as a white solid with an isomer ratio of SR:SS=3.1:96.9 and a yield of 22%. $^1$H NMR (400 MHz, DMSO-de) δ 8.00 (s, 1H), 7.74 (s, 1H), 6.06 (s, 2H), 3.71-3.62 (m, 2H), 2.89 (dd, J=12.3, 4.9 Hz, 1H), 2.75 (dd, J=12.0, 7.9 Hz, 1H), 2.49-2.39 (m, 1H), 2.37-2.18 (m, 1H), 2.11 (s, 1H), 1.83 (dd, J=12.4, 7.1 Hz, 2H), 1.27 (s, 4H), 0.97-0.66 (m, 6H).

Example 9: Preparation of Brivaracetam (I)

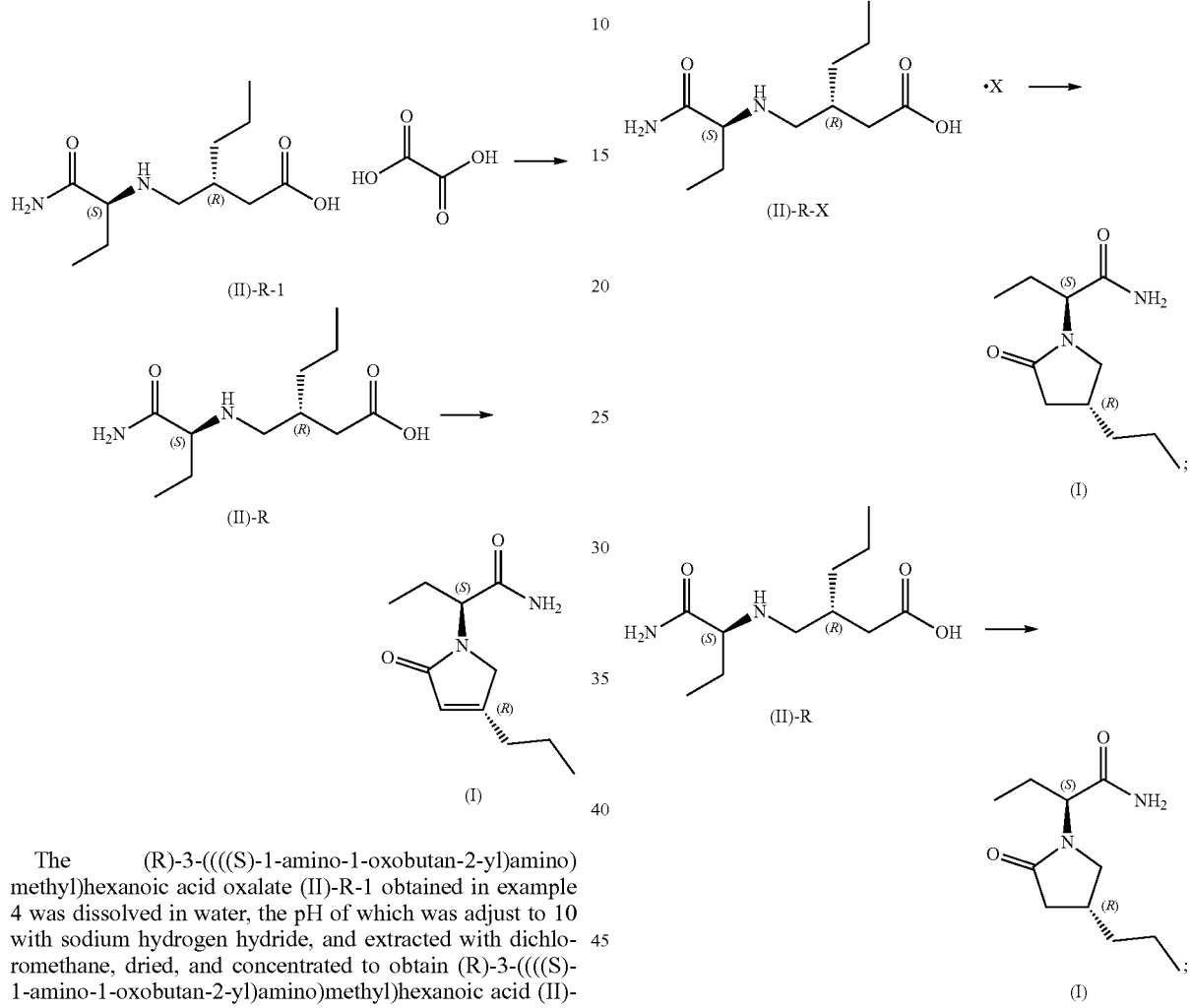

The (R)-3-((((S)-1-amino-1-oxobutan-2-yl)amino) methyl)hexanoic acid oxalate (II)-R-1 obtained in example 4 was dissolved in water, the pH of which was adjust to 10 with sodium hydrogen hydride, and extracted with dichloromethane, dried, and concentrated to obtain (R)-3-((((S)-1-amino-1-oxobutan-2-yl)amino)methyl)hexanoic acid (II)-R.

5.0 g of (R)-3-((((S)-1-amino-1-oxobutan-2-yl)amino) methyl)hexanoic acid (II)-R with an isomer ratio of SR:SS=99.8:0.2 was dissolved in 30 mL of isopropanol, then it was heated to reflux for 4 hours, and concentrated under reduced pressure; the obtained crude product was dissolved in 5.0 mL of ethyl acetate, and 25 mL of n-heptane was added dropwise, and it was stirred at room temperature for crystallization for 1 hour, and filtered by suction filtration, and rinsed with n-heptane and dried to obtain 4.3 g of brivaracetam (I) with an isomer ratio of SR:SS=99.8:0.2 and a yield of 93.2%. See example 5 for structural identification data.

Although the specific embodiments of the present invention are described above, those skilled in the art should understand that these are only embodiments, and various changes or modifications may be made to these embodiments without departing from the principle and essence of the present invention. Therefore, the protection scope of the present invention is defined by the appended claims.

What is claimed is:

1. A method for preparing brivaracetam represented by formula (I), comprising the following steps: in a solvent, carrying out a cyclization reaction with the compound represented by formula (II)-R-X or (II)-R as shown below; wherein, X is an organic acid;

the solvent is one or more of water, alcohol solvents and thionyl chloride.

2. The method for preparing brivaracetam represented by formula (I) as defined in claim 1, wherein, the X is oxalic acid or maleic acid;

or, the molar concentration of the compound represented by formula (II)-R-X or (II)-R in the solvent is 0.4-0.8 mol/L;

or, the temperature of the cyclization reaction is 65-80° C.;

or, the time of the cyclization reaction is 4-10 h.

3. The method for preparing brivaracetam represented by formula (I) as defined in claim 1, further comprising the following steps: under the action of a base, dissociating the compound represented by formula (II)-R-X to obtain the compound represented by formula (II)-R;

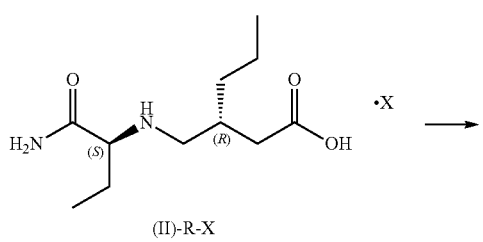

(II)-R-X

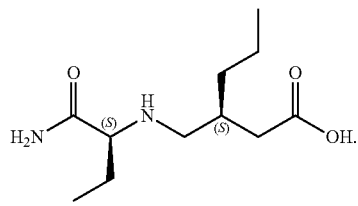

(II-S)

5. The method for preparing brivaracetam represented by formula (I) as defined in claim 4, wherein,
the X is oxalic acid or maleic acid;
or, in the salification reaction step, the solvent is $C_{1-4}$ alcohol and/or water;
or, in the salification reaction step, the mass ratio of the solvent to the compound represented by formula (II) is 4:1;
or, the molar ratio of the compound represented by formula (II) to the X is (1-1.3):1;
or, in the crystallization step, the solvent is a mixed solvent of $C_{1-4}$ alcohol, water and ether solvent, or a mixed solvent of $C_{1-4}$ alcohol, water and alkane solvent;
or, in the crystallization step, the mass ratio of the solvent to the compound represented by formula (II) is (7-11):1;
or, the temperature of the crystallization is 25-30° C.;
or, the crystallization time of the crystallization step is 1-2 h.

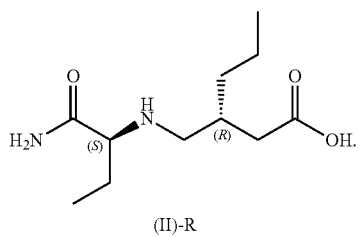

(II)-R

4. The method for preparing brivaracetam represented by formula (I) as defined in claim 1, further comprising the following steps: carry out a salification reaction between the compound represented by formula (II) and X, and then crystallizing to obtain the compound represented by formula (II)-R-X; wherein, X is an organic acid;

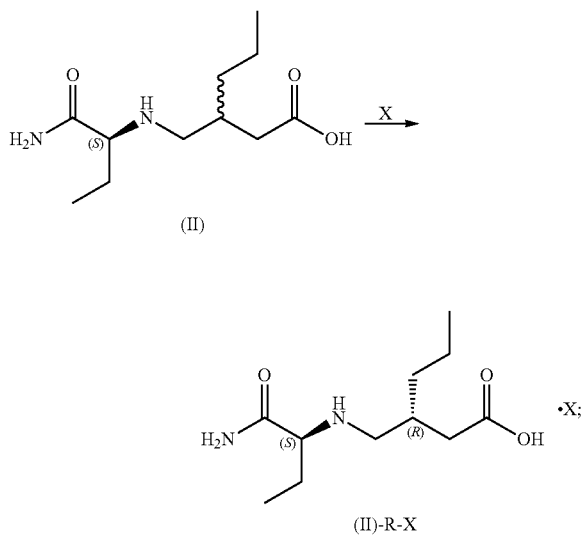

the compound represented by formula (II) is (II)-R or a mixture of (II)-R and (II)-S at any ratio;

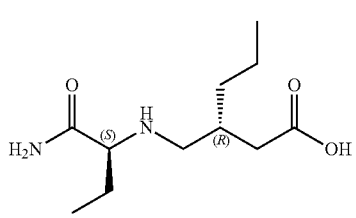

(II-R)

6. The method for preparing brivaracetam represented by formula (I) as defined in claim 5, wherein,
the $C_{1-4}$ alcohol is one or more of isopropanol, n-butanol and isobutanol;
or, the ether solvent is petroleum ether and/or isopropyl ether;
or, the alkane solvent is n-hexane and/or n-heptane;
or, in the crystallization step, the mass ratio of the $C_{1-4}$ alcohol, water and (ether solvent or alkane solvent) is 4:1:(4-6).

7. The method for preparing brivaracetam represented by formula (I) as defined in claim 4, wherein, in the crystallization step, the solvent is a mixed solvent of isobutanol, water and isopropyl ether, or a mixed solvent of isopropanol, water and isopropyl ether.

8. The method for preparing brivaracetam represented by formula (I) as defined in claim 4, further comprising the following steps: adding the compound represented by formula (II) to a mixed solvent of C1-4 alcohol and water, and then adding an organic acid, ether or alkane solvent in sequence, and crystallizing.

9. The method for preparing brivaracetam represented by formula (I) as defined in claim 4, further comprising the following steps: adding the compound represented by formula (II) to a mixed solvent of $C_{1-4}$ alcohol and water, and then adding an organic acid, ether or alkane solvent in sequence, crystallizing, and adding the product obtained by crystallization to a mixed solvent of $C_{1-4}$ alcohol and water, and then adding ether or alkane solvent, and crystallizing.

10. The method for preparing brivaracetam represented by formula (I) as defined in claim 4, further comprising the following steps: in a solvent, under the action of a catalyst, carrying out a hydrogenation reduction reaction between the compound represented by formula (III) and hydrogen as shown below to obtain the compound represented by formula (II);

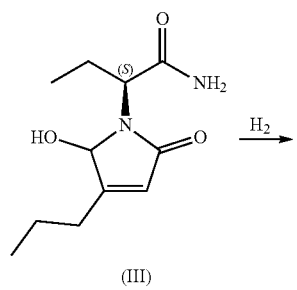

(III)

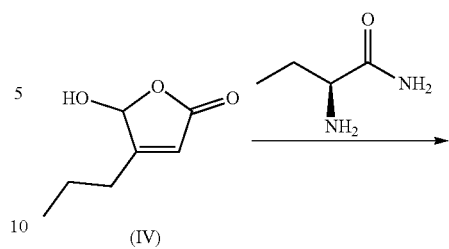

(IV)

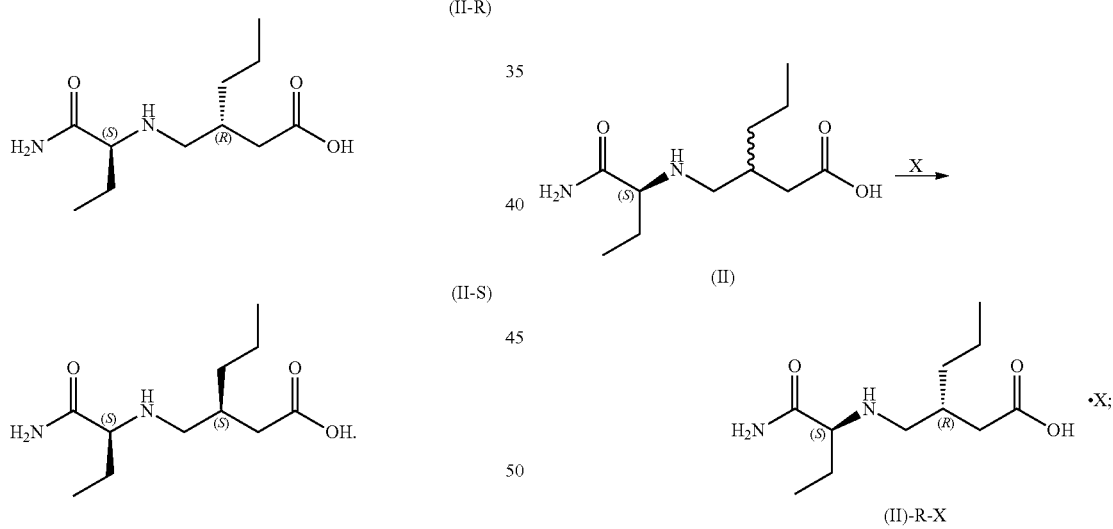

the compound represented by formula (II) is (II)-R, (II)-S, or a mixture thereof at any ratio;

11. The method for preparing brivaracetam represented by formula (I) as defined in claim 10, wherein, the hydrogenation reduction reaction is carried out with the participation of an organic acid, and the organic acid is citric acid;

or, the molar ratio of the organic acid to the compound represented by formula (III) is (7-10):1.

12. The method for preparing brivaracetam represented by formula (I) as defined in claim 10, further comprising the following steps: in a solvent, carrying out a reaction between the compound represented by formula (IV) and L-aminobutanamide as shown below to obtain the compound represented by formula (III),

13. A method for preparing a compound represented by formula (II)-R-X, comprising the following steps: carrying out a salification reaction between the compound represented by formula (II) and X, then crystallizing to obtain the compound represented by formula (II)-R-X; wherein, X is an organic acid;

the compound represented by formula (II) is (II)-R or a mixture of (II)-R and (II)-S at any ratio;

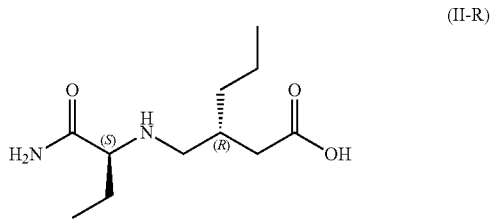

(II-R)

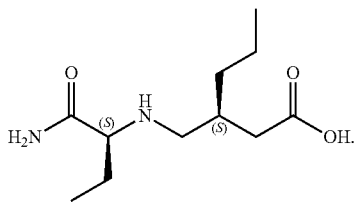
(II-S)

14. A method for preparing a compound represented by formula (II)-S-X, comprising the following steps:
(i) carrying out a salification reaction between the compound represented by formula (II) and X, then crystallizing to obtain a compound represented by formula (II)-R-X;
(ii) adding X and solvent to the mother liquor after crystallization in step (i), and crystallizing;

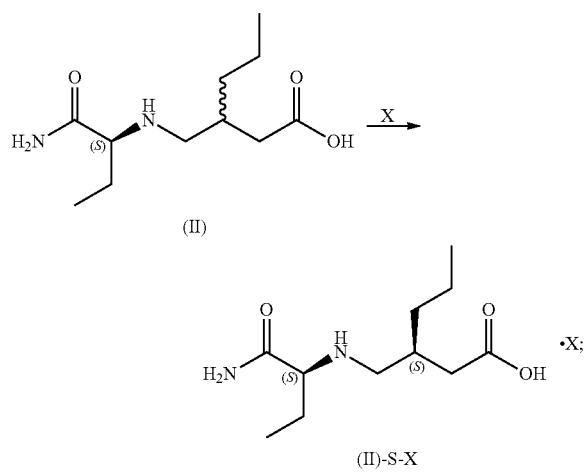

wherein, the X is an organic acid;
the compound represented by formula (II) is a mixture of (II)-R and (II)-S at any ratio;

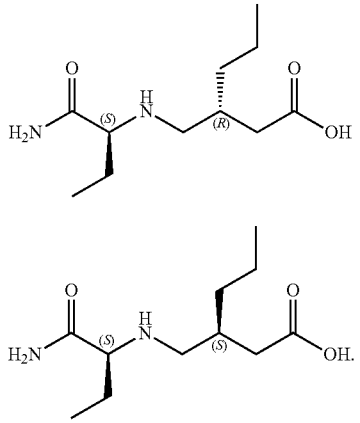

15. The method for preparing the compound represented by formula (II)-S-X as defined in claim 14, wherein,
the X is oxalic acid or maleic acid;
or, in step (ii), the solvent is petroleum ether and/or isopropyl ether;

or, in step (ii), the molar ratio of the X to the compound represented by the formula (II) is 1:(1-4);

or, in step (ii), the volume-to-mass ratio of the solvent to the compound represented by formula (II) is (1-4) mL/g;

or, in step (ii), the temperature of the crystallization is −20-0° C.

16. A method for preparing a compound represented by formula (II), comprising the following steps: in a solvent, under the action of a catalyst, carrying out a hydrogenation reduction reaction between the compound represented by formula (III) and hydrogen as shown below to obtain the compound represented by formula (II);

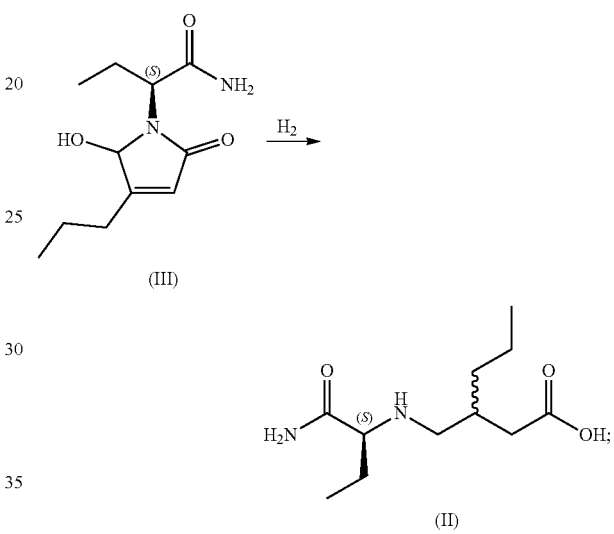

the compound represented by formula (II) is (II)-R, (II)-S, or a mixture thereof at any ratio;

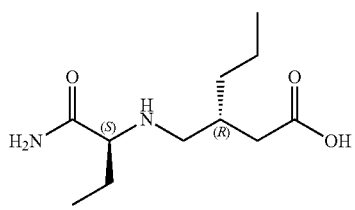

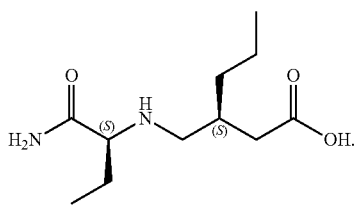

17. The method for preparing the compound represented by formula (II) as defined in claim 16, further comprising the following steps: in a solvent, carrying out a reaction between the compound represented by formula (IV) and L-aminobutanamide as shown below to obtain the compound represented by formula (III),

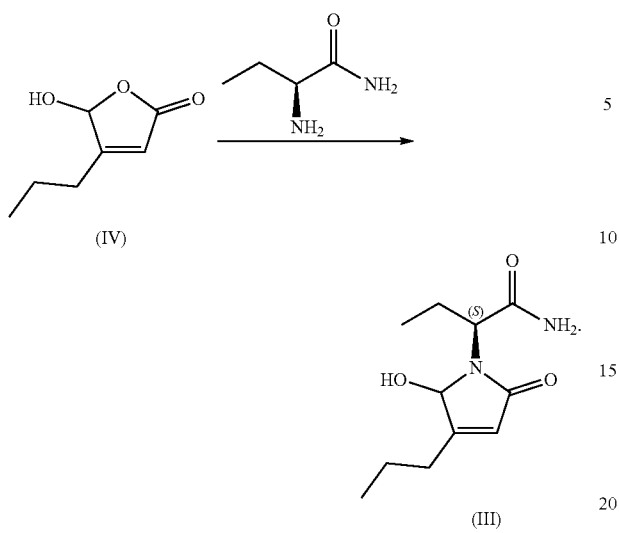
18. A method for preparing brivaracetam represented by formula (I) as defined in claim 1, wherein, the solvent is $C_{1-4}$ alcohol.
19. A method for preparing brivaracetam represented by formula (I) as defined in claim 18, wherein, the solvent is one or more of methanol, ethanol and isopropanol.
* * * * *